(12) United States Patent
Chauvin et al.

(10) Patent No.: US 7,828,848 B2
(45) Date of Patent: Nov. 9, 2010

(54) EXPANDABLE OSTEOSYNTHESIS CAGE

(75) Inventors: Jean-Luc Chauvin, Uchaux (FR); David Attali, Avignon (FR); David Attia, Montecimar (FR)

(73) Assignee: Wenzel Spine, Inc., Austin, TX (US)

( * ) Notice: Subject to any disclaimer, the term of this patent is extended or adjusted under 35 U.S.C. 154(b) by 887 days.

(21) Appl. No.: 10/124,044

(22) Filed: Apr. 16, 2002

(65) Prior Publication Data
US 2002/0116066 A1 Aug. 22, 2002

Related U.S. Application Data

(63) Continuation of application No. 09/587,596, filed on Jun. 5, 2000, now Pat. No. 6,371,989, which is a continuation of application No. 09/117,469, filed as application No. PCT/FR97/01617 on Sep. 12, 1997, now Pat. No. 6,129,763.

(30) Foreign Application Priority Data
Sep. 13, 1996 (FR) .................................. 96 11452

(51) Int. Cl.
*A61F 2/44* (2006.01)
(52) U.S. Cl. .................... 623/17.16; 606/313; 606/314; 606/321; 606/323
(58) Field of Classification Search ... 623/17.11–17.16; 606/300–331; 411/395, 396, 397, 411, 418, 411/32, 913; 433/173, 174
See application file for complete search history.

(56) References Cited

U.S. PATENT DOCUMENTS 1,286,285 A 12/1918 Girvan
(Continued)

FOREIGN PATENT DOCUMENTS

DE 24 60 431 6/1976
(Continued)

OTHER PUBLICATIONS

Mayo Clinic, vol. 61, Feb. 1987, "Dental Implants: Tissue-Integrated Prosthesis Utilizing the Osseointegration Concept".
(Continued)

*Primary Examiner*—Eduardo C Robert
*Assistant Examiner*—Mary Hoffman
(74) *Attorney, Agent, or Firm*—Trop, Pruner & Hu, P.C.

(57) ABSTRACT

An expandable osteosynthesis implant has branches each connected at one end to a seat which is pierced by an orifice, suitable for being slid from a posterior direction between the facing faces of two consecutive vertebrae in order to hold them a given distance apart and restore stability of the spinal column. The branches and the seat define a hollow cage which, in a "rest" position, has an outside general shape that is a cylinder of circular section, and a portion at least of the inside volume of the cage towards the distal ends of the branches is in the form of a circular truncated cone whose large base is towards the seat, which implant has at least three branches and, inside the inside volume at least one spacer suitable for passing through the orifice and the large base of the truncated cone.

15 Claims, 5 Drawing Sheets

U.S. PATENT DOCUMENTS

| | | | |
|---|---|---|---|
| 2,490,364 A | 12/1949 | Livingston | |
| 2,587,907 A | 3/1952 | Schroeder et al. | |
| 2,721,387 A | 10/1955 | Aschuckian | |
| 3,435,526 A | 4/1969 | Brancato | |
| 3,499,222 A | 3/1970 | Linkow el al. | |
| 3,579,831 A | 5/1971 | Stevens et al. | |
| 3,708,883 A | 1/1973 | Flander | |
| 3,848,601 A | 11/1974 | Ma et al. | |
| 3,905,109 A | 9/1975 | Cohen et al. | |
| 4,011,602 A | 3/1977 | Rybicki et al. | |
| 4,013,071 A | 3/1977 | Rosenberg | |
| 4,349,921 A | 9/1982 | Kuntz | |
| 4,431,416 A | 2/1984 | Niznick | |
| 4,484,570 A | 11/1984 | Sutter et al. | |
| 4,501,269 A | 2/1985 | Bagby | |
| 4,523,587 A | 6/1985 | Frey | |
| 4,588,381 A | 5/1986 | Caracciolo | |
| 4,714,469 A | 12/1987 | Kenna | |
| 4,722,688 A | 2/1988 | Lonca | |
| 4,743,256 A | 5/1988 | Brantigan | |
| 4,834,757 A | 5/1989 | Brantigan | |
| 4,877,020 A | 10/1989 | Vich | |
| 4,878,915 A | 11/1989 | Brantigan | |
| 4,932,868 A | 6/1990 | Linkow et al. | |
| 4,936,848 A | 6/1990 | Bagby | |
| 4,961,740 A | 10/1990 | Ray et al. | |
| 5,004,421 A | 4/1991 | Lazarof | |
| 5,013,242 A | 5/1991 | Prezmecky | |
| 5,015,247 A | 5/1991 | Michelson | |
| 5,017,067 A | 5/1991 | Ohlin | |
| 5,023,990 A | 6/1991 | Lee, II et al. | |
| 5,026,373 A | 6/1991 | Ray et al. | |
| 5,055,104 A | 10/1991 | Ray | |
| 5,059,193 A | 10/1991 | Kuslich | |
| 5,061,181 A | 10/1991 | Niznick | |
| 5,087,199 A | 2/1992 | Lazarof | |
| 5,108,395 A | 4/1992 | Laurain | |
| 5,192,327 A | 3/1993 | Brantigan | |
| 5,209,753 A | 5/1993 | Biedermann et al. | |
| 5,217,497 A | 6/1993 | Mehdian | |
| 5,259,398 A | 11/1993 | Vrespa | |
| 5,269,685 A | 12/1993 | Jorneus et al. | |
| 5,282,861 A | 2/1994 | Kaplan | |
| 5,360,450 A | 11/1994 | Giannini | |
| 5,390,683 A | 2/1995 | Pisharodi | |
| 5,397,364 A | 3/1995 | Kozak et al. | |
| 5,443,514 A | 8/1995 | Steffee | |
| 5,458,638 A | 10/1995 | Kuslich et al. | |
| 5,470,230 A * | 11/1995 | Daftary et al. ............... 433/174 |
| 5,474,555 A | 12/1995 | Puno et al. | |
| 5,484,437 A | 1/1996 | Michelson | |
| 5,489,210 A | 2/1996 | Hanosh | |
| 5,505,732 A | 4/1996 | Michelson | |
| 5,522,899 A | 6/1996 | Michelson | |
| 5,554,191 A | 9/1996 | Lahille et al. | |
| 5,591,235 A | 1/1997 | Kuslich | |
| 5,593,409 A | 1/1997 | Michelson | |
| 5,609,635 A | 3/1997 | Michelson | |
| 5,609,636 A | 3/1997 | Kohrs et al. | |
| 5,611,688 A | 3/1997 | Hanosh | |
| 5,653,763 A | 8/1997 | Errico et al. | |
| 5,658,285 A | 8/1997 | Marnay et al. | |
| 5,665,122 A | 9/1997 | Kambin | |
| 5,669,909 A | 9/1997 | Zdeblick et al. | |
| 5,681,167 A | 10/1997 | Lazarof | |
| 5,683,394 A | 11/1997 | Rinner | |
| 5,702,393 A | 12/1997 | Pfaifer | |
| 5,702,397 A | 12/1997 | Goble et al. | |
| 5,707,395 A | 1/1998 | Li | |
| 5,713,904 A | 2/1998 | Errico et al. | |
| 5,723,013 A | 3/1998 | Jeanson et al. | |
| 5,725,529 A | 3/1998 | Nicholson et al. | |
| 5,725,581 A | 3/1998 | Branemark | |
| 5,741,253 A | 4/1998 | Michelson | |
| 5,749,916 A | 5/1998 | Richelsoph | |
| 5,762,500 A | 6/1998 | Lazarof | |
| 5,766,252 A | 6/1998 | Henry et al. | |
| 5,772,661 A | 6/1998 | Michelson | |
| 5,776,197 A | 7/1998 | Rabbe et al. | |
| 5,776,198 A | 7/1998 | Rabbe et al. | |
| 5,782,865 A | 7/1998 | Grotz | |
| 5,785,710 A | 7/1998 | Michelson | |
| 5,797,909 A | 8/1998 | Michelson | |
| 6,080,155 A | 6/2000 | Michelson | |
| 6,083,228 A | 7/2000 | Michelson | |
| 6,096,038 A | 8/2000 | Michelson | |
| 6,102,950 A | 8/2000 | Vaccaro | |
| 6,117,174 A | 9/2000 | Nolan | |
| 6,120,503 A | 9/2000 | Michelson | |
| 6,123,705 A | 9/2000 | Michelson | |
| 6,139,551 A | 10/2000 | Michelson et al. | |
| 6,149,650 A | 11/2000 | Michelson | |
| 6,179,873 B1 | 1/2001 | Zientek | |
| 6,190,388 B1 | 2/2001 | Michelson et al. | |
| 6,190,414 B1 | 2/2001 | Young | |
| 6,206,923 B1 | 3/2001 | Boyd | |
| 6,210,412 B1 | 4/2001 | Michelson | |
| 6,214,050 B1 | 4/2001 | Huene | |
| 6,224,595 B1 | 5/2001 | Michelson | |
| 6,264,656 B1 | 7/2001 | Michelson | |
| 6,270,498 B1 | 8/2001 | Michelson | |
| 6,302,914 B1 | 10/2001 | Michelson | |
| 6,350,283 B1 | 2/2002 | Michelson | |
| 6,395,031 B1 | 5/2002 | Foley | |
| 6,436,140 B1 | 8/2002 | Liu | |
| 6,436,142 B1 | 8/2002 | Paes | |
| 6,447,544 B1 | 9/2002 | Michelson | |
| 6,471,724 B2 | 10/2002 | Zdeblick | |
| 6,491,724 B1 | 12/2002 | Ferree | |
| 6,579,290 B1 | 6/2003 | Hardcastle | |
| 6,719,796 B2 | 4/2004 | Cohen | |
| 6,962,606 B2 | 11/2005 | Michelson | |
| 6,972,035 B2 | 12/2005 | Michelson | |
| 2004/0044409 A1 | 3/2004 | Alfaro | |

FOREIGN PATENT DOCUMENTS

| | | |
|---|---|---|
| DE | 77 01 056 | 1/1977 |
| DE | 25 42 263 | 3/1977 |
| DE | 36 15 091 | 11/1987 |
| DE | 43 23 956 | 7/1993 |
| DE | 94 07 806 | 11/1994 |
| DE | 44 16 605 | 6/1995 |
| EP | 0493789 | 7/1992 |
| EP | 0 595 782 | 5/1994 |
| EP | 0 637 440 | 2/1995 |
| EP | 0 664 994 | 8/1995 |
| EP | 0 734 703 | 10/1996 |
| FR | 94 00860 | 1/1994 |
| FR | 2 719 763 | 8/1995 |
| GB | 86 20937 | 8/1986 |
| GB | 2 181 809 | 4/1987 |
| GB | 2294399 | 1/1996 |
| JP | 60-43984 | 10/1985 |
| JP | 63-145650 | 6/1988 |
| JP | 63-300758 | 12/1988 |
| JP | 2-149271 | 6/1990 |
| JP | 3-503133 | 7/1991 |
| JP | 3-52742 | 8/1991 |
| JP | 3-63898 | 10/1991 |
| JP | 3-505416 | 11/1991 |
| JP | 3-275055 | 12/1991 |
| JP | 4-20342 | 1/1992 |
| JP | 4-42940 | 7/1992 |

| | | |
|---|---|---|
| JP | 4-88929 | 8/1992 |
| JP | 5-51304 | 8/1993 |
| JP | 5-52218 | 8/1993 |
| JP | 5-269160 | 10/1993 |
| JP | 6-189991 | 7/1994 |
| JP | 6-237944 | 8/1994 |
| JP | 6-319759 | 11/1994 |
| JP | 7-7612 | 2/1995 |
| JP | 7-39557 | 2/1995 |
| JP | 7-148189 | 6/1995 |
| JP | 7-148190 | 6/1995 |
| JP | 7-275267 | 10/1995 |
| JP | 8-56971 | 3/1996 |
| JP | 8-503876 | 4/1996 |
| JP | 8-215225 | 8/1996 |
| JP | 2551670 | 8/1996 |
| JP | 8-226564 | 10/1996 |
| JP | 8-266563 | 10/1996 |
| JP | 8-266565 | 10/1996 |
| JP | 8-294495 | 11/1996 |
| JP | 8-511701 | 12/1996 |
| JP | 2632850 | 4/1997 |
| JP | 9-506790 | 7/1997 |
| JP | 2669379 | 7/1997 |
| JP | 10-33656 | 2/1998 |
| JP | 10-99356 | 4/1998 |
| JP | 2769926 | 4/1998 |
| JP | 10-165412 | 6/1998 |
| JP | 10-501710 | 7/1998 |
| RU | 2008851 | 3/1994 |
| WO | WO 88/03781 | 2/1988 |
| WO | WO 93/02077 | 10/1993 |
| WO | 97/08205 | 3/1995 |
| WO | WO 96/08205 | 2/1996 |
| WO | WO 96/16607 | 6/1996 |

OTHER PUBLICATIONS

Int. J. Oral Surg. 1981—Review Article, "A 15-year study of osseointegrated implants in the treatment of the edentulous jaw".
U.S. Appl. No. 09/951,751, titled Method and Apparatus for Providing Proper Vertebral Spacing, filed Sep. 11, 2001.
U.S. Appl. No. 11/448,335, titled Method and Apparatus for Providing Proper Vertebral Spacing, filed Jun. 7, 2006.
U.S. Appl. No. 09/587,596, filed Jun. 5, 2000; Notice of Allowance Aug. 30, 2001.
U.S. Appl. No. 09/951,751, filed Sep. 11, 2001, Office Actions sent Sep. 29, 2003; Feb. 10, 2004; Jun. 14, 2005; Nov. 15, 2005; Feb. 8, 2006; Nov. 2, 2006; and May 22, 2007.
U.S. Appl. No. 10/124,044, filed Apr. 16, 2002; Office Actions sent Sep. 3, 2004; Apr. 5, 2006 and Apr. 5, 2007.

* cited by examiner

EXPANDABLE OSTEOSYNTHESIS CAGE

This is a continuation of U.S. patent application Ser. No. 09/587,596, filed Jun. 5, 2000 (now U.S. Pat. No. 6,371,989), which is a continuation of U.S. patent application Ser. No. 09/117,469, filed on Jul. 28, 1998 (now U.S. Pat. No. 6,129,763), which claims priority to PCT Application No. PCT/FR97/01617, filed on Sep. 12, 1997, which claims priority to French Patent Application No. 96/11452, filed on Sep. 13, 1996.

FIELD OF THE DISCLOSURE

The present invention relates to an expandable osteosynthesis cage.

The technical field of the invention is that of implantable bone implants or prostheses and the surgical techniques for using them.

The main application of the invention is to provide implants designed to be slid or inserted from a posterior direction between the facing faces of two consecutive vertebrae in order to maintain a given distance between them and to restore the stability of the spinal column, e.g. after a failure of the corresponding joint, by fixing the two vertebrae together.

BACKGROUND

Several techniques are known at present for restoring a "normal" lumbar lordosis in this way, by implanting either a graft which in time fuses the vertebrae together, or a prosthesis which fixes them together immediately, while still also making it possible in time to achieve fusion between the vertebra.

In the second above-mentioned technique, use is made mainly of implants, also known as "cages", some of which are hollow, rigid, and one-piece, with inside/outside intercommunication slots for receiving a bone graft which, via said slots, subsequently fuses with the adjacent vertebrae on either side: in this field, reference can be made to patent application WO 96/08205 published on Mar. 21, 1996 for a "Intervertebral fusion cage of conical shape" and application EP 637 440 published on Feb. 8, 1995 for an "Intersomatic implant for the spinal column". Nevertheless, cages of those types are of outside dimensions that are given and fixed, whereas the distances between pairs of vertebrae are not constant. In addition, the inclinations of the facing vertebral faces to which a given angular position is to be imparted do not enable rigid cages to be used from a posterior direction: they can be inserted only from an anterior direction.

As a result, other types of cage have been developed with two substantially parallel branches connected to a rigid body through which it is possible to turn a wormscrew system which then moves a wedge in screw engagement on said screw from an initial position close to the distal ends of the branches towards the body linking the branches together, thereby splaying the two branches apart angularly. It is then possible to insert such a cage of initially flat shape between the vertebrae, and then by turning the drive axis of the wedge, the desired angle between the branches is adjusted or set from a posterior access.

Such cages or implants are described, for example, in European patent application EP 664 994 published on Aug. 2, 1995, entitled "Vertebral intersomatic cage" or in application EP 2 719 763 published on Nov. 17, 1995, and entitled "Vertebral implant".

Nevertheless, such devices which are more mechanical than hollow and rigid cages, and therefore more complex, leave a smaller inside volume for the fusion graft, and because of their flat shape which is not circularly symmetrical, even though they are better at ensuring a given bearing angle between the vertebrae, they require a passage of the same rectangular section to be prepared to receive them, and that complicates implementation.

SUMMARY

The problem posed is thus to be able to have implants or cages available making it possible simultaneously to ally the shape of a conventional rigid cage, firstly to facilitate implantation and secondly to provide a larger inside volume, with the possibility of increasing the diameter of the distal end of the cage to a given value relative to its end situated adjacent to its point of surgical insertion, after it has been put into place, and corresponding to the posterior face of the vertebrae, while having as few mechanical elements as possible.

A solution to the problem posed is an expandable osteosynthesis implant having branches each connected at one end to a seat pierced by an orifice, such that said branches and the seat constitute a hollow cage which, in a "rest" position, has an outside general shape that is cylindrical or quasi-cylindrical with the generator line that generates it by rotating about its axis of symmetry being either a straight line or having a curved middle portion such as a convex circular arc of large radius, and having a director curve around which the generator line travels, thus also defining the cross-section of the cylinder, which is quasi-circular: this provides a cylinder that is either a right circular cylinder or else a cylinder that is referred to in the present case as being "ovoid" or "oval", and which is referred to below as being a cylinder or a quasi-cylinder; a portion at least of the inside volume of the cage towards the distal ends of the branches is in the form of a quasi-circular truncated cone whose large base is towards said seat, said implant having at least three branches and at least one spacer of dimensions compatible with the dimensions of the large base of the truncated cone in said inside volume in the rest position, and possibly suitable for passing through said orifice.

In an "active" position, said spacer splays said branches apart, said inside volume tends towards a circular cylinder, and the outside shape of the cage tends towards an approximate truncated cone, and once the spacer has been put into the desired position, no internal part remains inside the space defined by said branches, the spacer, and the orifice.

The definitions of the "rest" and "active" positions are shown by way of example respectively in FIGS. 1, 3A, 4A, 5A, 9, 10, and 11, and in FIGS. 2, 3B, 3C, 4B, and 5B. The "rest" position is the position of the implant before it is put into place and while it is being put into place, i.e. without the spacer positioned between its branches inside the cage, so the cage has a cylindrical outside volume of constant section. The "active" position is the final position of the implant, e.g. between two vertebrae, with its branches splayed apart by the spacer being placed in its final adjustment position, the general outside shape of the cage then being approximately frustoconical, flaring away from the seat, which corresponds to the end of the implant situated towards its point of surgical insertion, towards its distal end which is placed in deeper between the vertebrae.

To provide better anchoring in the bone and to avoid any subsequent migration of the cage, the outside surfaces of said branches are preferably either knurled, grooved, or threaded using a thread profile having projecting ridges, etc.

Also, to reduce any risk of rotation after implantation, and thus reduce any risk of displacement of the cage, while simultaneously increasing contact area with the faces of the vertebrae, at least the seat of the implant and preferably also the sides of the branches have at least two optionally parallel flats, each disposed symmetrically about the axis of the implants between two successive branches. These flats, optionally assisted by the generally ovoid shape of the cage, make better retention possible after expansion by reducing any risk of the implant rotating. In addition, said ovoid shape can make it possible, better than if the outer generator line of the basic cylindrical shape of the cage at rest were a straight line, to return after expansion to an outside profile that is conical and without curvature, thereby providing better-distributed thrust against the body of the vertebrae, thus helping the bone graft to take better.

To stiffen the cage at its posterior end, particularly if there is a large orifice in the seat, thereby making it easier to fill the cage with bone matter after the cage has been put into place and expanded, the orifice of said seat is suitable for receiving a plug for closing the inside volume of the cage. By way of example, the plug can be screwed into said orifice, in which case the orifice is also threaded. Under such circumstances, the plug prevents bone matter from escaping and depending on the material out of which it is made, it can also stiffen the cage.

Various particular embodiments are described below in the accompanying figures. The result is novel expandable osteosynthesis implants satisfying the problem posed, in particular for the above-defined main application.

The presence of at least four branches, and possibly four to eight branches, makes it possible to obtain bilateral expansion, and thereby better jamming against the two facing faces of the vertebrae, and the absence of a link part or rod between the spacer maintaining said expansion and the orifice or plug in the end seat guarantees a larger inside volume for receiving a large quantity of bone matter, thereby improving consolidation and joining by fusion, in particular between the vertebrae that are to be held together. Said filling operation is made that much easier by having a large orifice at the posterior end of the cage through said seat.

In addition, said orifice makes it possible to scrape the faces of the vertebrae through the slots situated between the branches in the bottom and top faces of the cage.

Furthermore, the expansion system as defined above is very simple, since it comprises only two parts, namely the spacer and the cage (optionally having a plug situated at its end and possibly also having an intermediate spacer, as mentioned-below) but no link member remaining after installation, since any rod or shaft for positioning said spacers and said plug is subsequently removed.

The present invention thus provides numerous advantages over existing implants or cages, of the kind already mentioned, and other advantages can also be provided but those given above suffice to demonstrate the novelty and the usefulness of the invention.

The description and the figures below show two embodiments of the invention with four branches, but they are not limiting in any way: other embodiments are possible in the context of the ambit of the scope of this invention, for example embodiments with three branches or embodiments with more than four.

DETAILED DESCRIPTION

Figure 9:
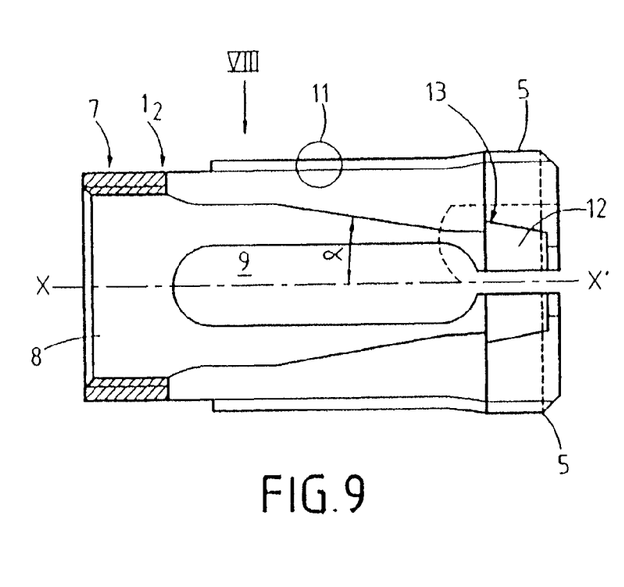
FIGS. 9, 10, and 11 are respectively a fragmentary side view, and two axial views showing the anterior face and the posterior face of the embodiment of the implant shown in perspective in FIGS. 1 and 2.
Figure 10:
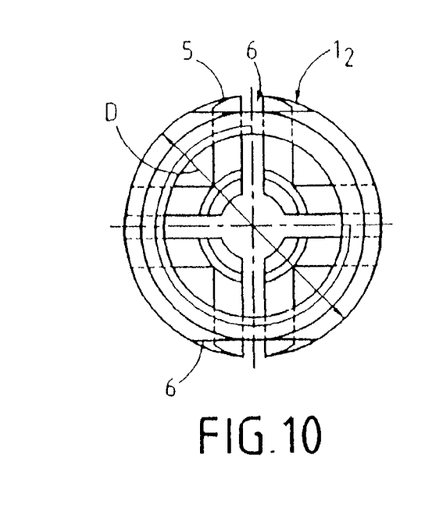
Figure 11:
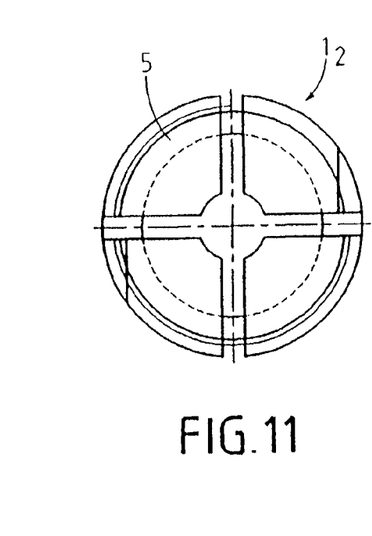

Whatever the embodiment, the expandable osteosynthesis implant comprises in conventional manner branches 5, each connected at one end to a seat 7 pierced by an orifice 8. According to an essential characteristic of the invention, said branches 5 and the seat 7 constitutes a hollow cage 1 which, in a "rest" position as shown for the embodiments of FIGS. 1, 3A, 4A, and 5A, and of FIGS. 9, 10, and 11, is of general outside shape that is cylindrical or quasi-cylindrical having a cross-section which is also the director curve of said cylinder that is circular or quasi-circular, with the generator line which engages said director curve and which generates the cylinder or quasi-cylinder by moving around its axis of symmetry XX' being either a straight line or a convex circular arc of large radius: this provides either a circularly-symmetrical right cylinder as shown in solid lines $20_1$ in FIG. 3A, or else a pseudo-cylinder referred to in the present specification as being "oval" or "ovoid", i.e. being of slightly bulging outside shape, as shown in long and short dashed lines $20_2$ in FIG. 3A. At least a portion of the inside volume 9 of the cage 1 towards the distal ends of the branches 5 is in the form of a truncated cone that is quasi-circularly symmetrical with its larger base being closer to said seat 7, which implant has at least four branches 5 and at least one spacer 2 suitable for passing through said orifice 8 and via the large base of the truncated cone into said inside volume 9.

Figure 3A:
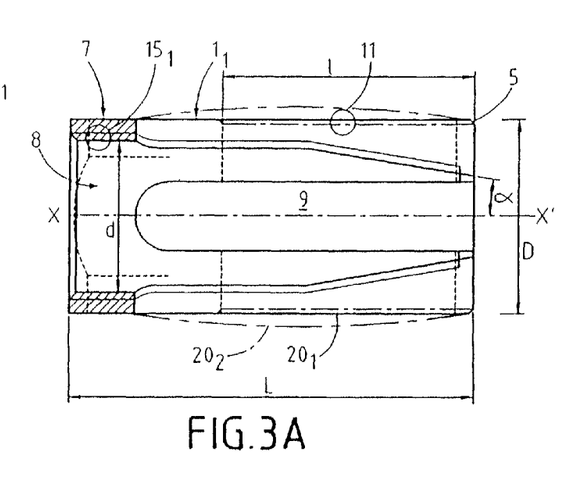
FIGS. 3A, 4A, and 5A are respectively a section view, and two axial end views, one of the anterior face and the other of the posterior face of a cage showing another embodiment of an implant of the invention in the "rest" position.
Figure 3B:
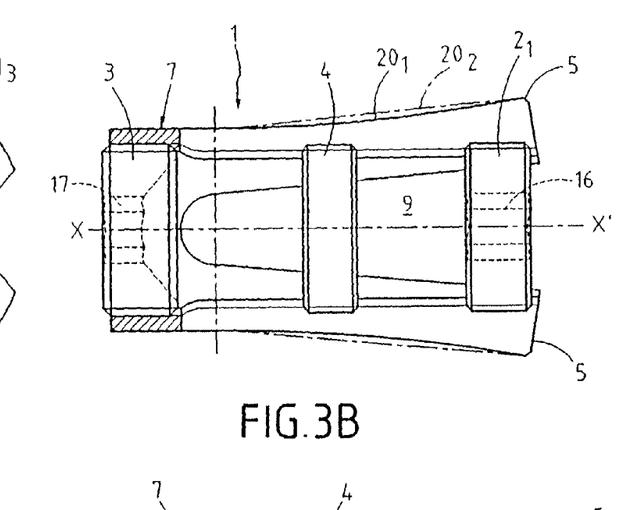
FIGS. 3B, 4B, and 5B show the same views as are shown in FIGS. 3A, 4A, and 5A, of the same cage, but with its complementary elements assembled together into the "active" position.
Figure 3C:
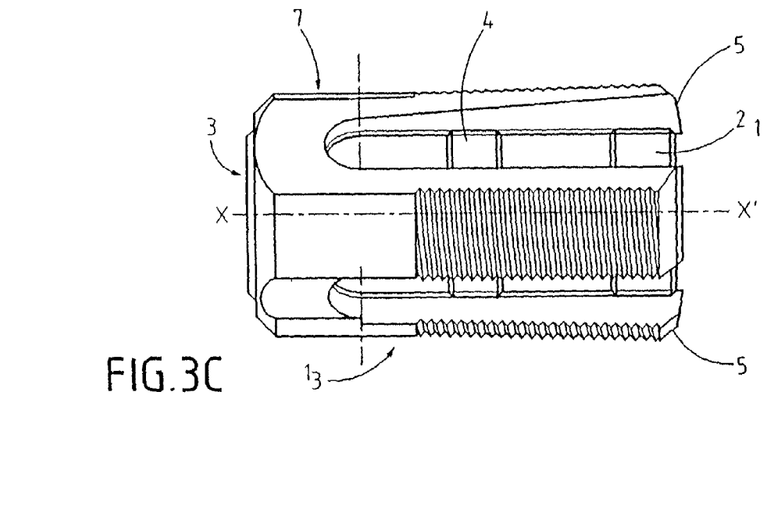
FIG. 3C is a side view perpendicular to the axis of the implant of the embodiment shown in FIGS. 3, 4, and 5, in the "active" position.
Figure 4A:
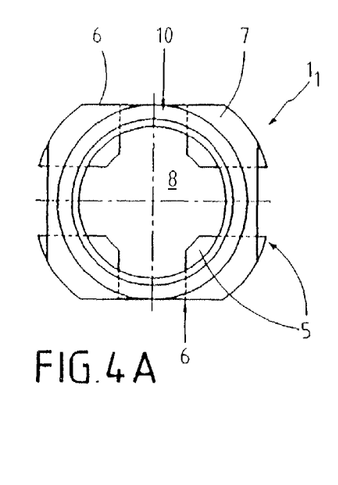
Figure 4B:
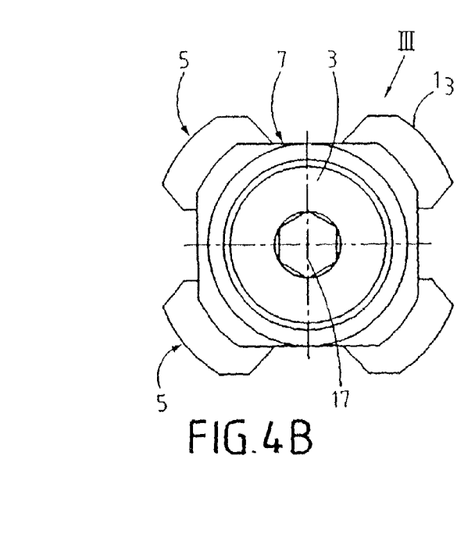
Figure 5A:
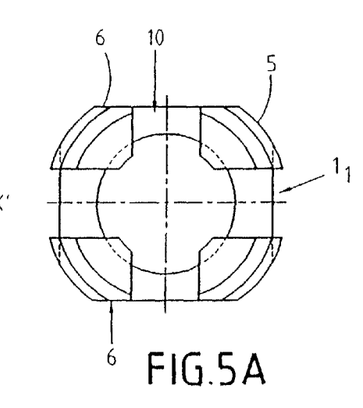
Figure 5B:
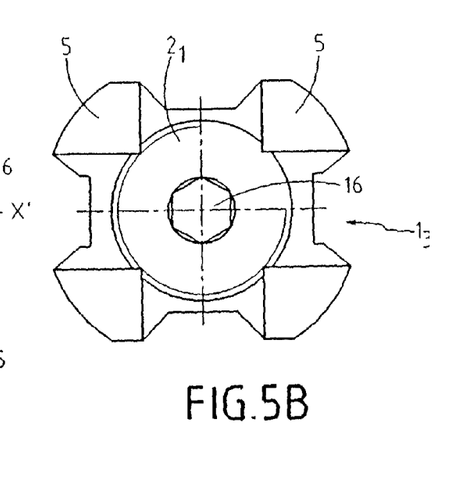

In FIGS. 2, 3B, 4B, 5B, and 3C, i.e. in the "active" position, said end spacer 2 spreads apart said branches 5, said inside volume 9 then tending towards a circular cylinder while the outside shape of the cage 1 tends towards an approximate truncated cone. In FIG. 3B, for example, solid lines $20_1$ show the slightly concave shape obtained from a regular base cylinder in the rest position while short and long dashed lines $20_2$ shows the straighter shape obtained from a cylinder that was initially ovoid, as shown in FIG. 3A. Once the spacer 2 has been placed in the desired position, no internal part that has been used for putting the implant and the spacers in place remains inside the space defined by said branches 5, the spacer 2, and the orifice 8.

Figure 7:
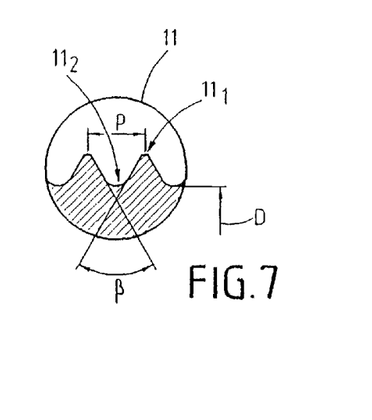

Whatever the embodiment, at least a portion of the outside surface of said branches 5 is threaded with a thread profile 11 having projecting ridges, as shown in detail in FIG. 7. In particular, by way of example, for a cage having a length L of about 20 mm to 25 mm, the length l of the threaded portion of the branches 5 may lie in the range 13 mm to 16 mm with a pitch p of 1.5 mm to 2 mm, the outside diameter D of the circular cylinder of the cage being 9 mm to 16 mm and the height of a tooth $11_1$ of the thread being of the order of 0.7 mm to 0.9 mm for a thread angle β between successive teeth being about 60°, and with an inside profile $11_2$ of the thread having a radius of about 0.4 mm. Said rounded shape of the profile minimizes stress concentrations, thus making it possible to withstand large forces and impacts.

Such an outside thread with projecting ridges thus facilitates installation since it is not traumatizing, given that there is no impact shock while inserting said implant since it is screwed into a hole previously bored by any tool compatible with the orifice 8 of the implant, and once in place such a thread also provides anchoring in the bone, thereby avoiding any subsequent migration.

The seat 7 may include at least two flats 6 that are parallel or slightly inclined relative to each other to fit the profile of vertebrae more closely, each disposed between two successive branches 5 as shown in the embodiments of FIGS. 1, 2, 9, 10, and 11. Alternatively, the seat 7 may have four flats forming a square or pseudo-square section, as shown in the embodiment of FIGS. 3, 4, and 5. In addition to the seat, the branches 5 themselves may also have respective flats at least in line with those of the seat, as shown in the embodiment of FIGS. 3 to 5, particularly if the section of the implant is quasi-circular, or alternatively may have no flats at all, as in the embodiment of FIGS. 1, 2 and 9 to 11. Such flats may be replaced or at least associated with a longitudinal implant section that is slightly oval or ovoid in shape, as mentioned above.

Figure 6:
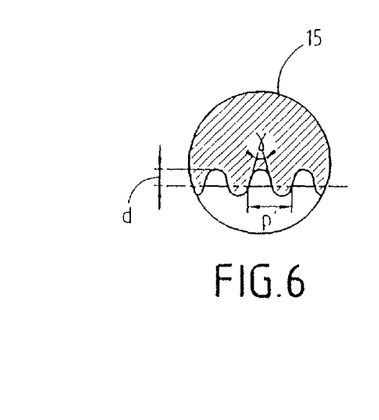
FIGS. 6, 7, and 8 are figures showing embodiment details of the cage of the implant of the invention.

The orifice 8 of the seat 7 can be threaded with a thread profile 15 as shown by way of example in FIG. 6, with a thread pitch that is rounded both at its ridges and in its furrows, and for association with the dimensions given above by way of example, an opening 8 may have an inside diameter d of 7 mm to 10 mm, a pitch p' of 1 mm to 1.5 mm, a thread depth of about 0.6 mm, and a thread angle γ between the walls of the thread of about 30°.

A plug 3 for closing the inside volume 9 is then screwed into said orifice 8, either to serve as an anchor point for an implant-installing rod, or else after the implant has been put into place and the branches have been splayed apart by the end spacer 2 for the purpose of closing the inside volume 9 in order firstly to stiffen the cage and secondly to prevent any bone matter that may have been implanted inside the cage from escaping via said posterior end.

Figure 14A:
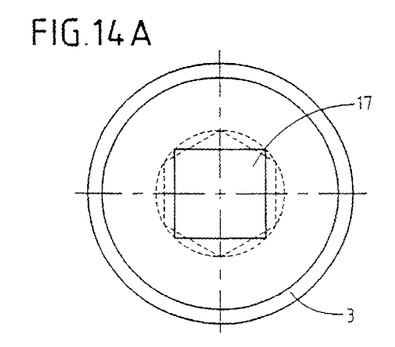
Figure 14B:
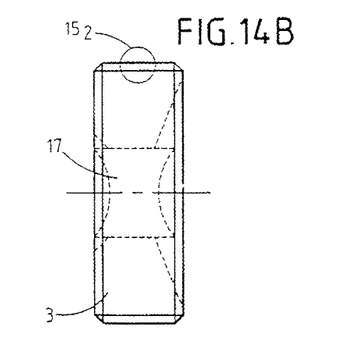

Such a plug 3 is shown in face view in FIG. 14A and in side view in FIG. 14B, having a thread $15_2$ of the type shown in FIG. 6 and a central orifice 17 of polygonal shape, being square, hexagonal, etc., or replaced by any means suitable for securing therein the end of a rod having a compatible end for the purpose of enabling the plug to be screwed and unscrewed.

In addition, it is possible to form on the posterior face of the implant and at the periphery of the orifice 8 in the seat 7, studs or grooves serving to secure a portion of the rod, enabling the cage 1, spacers, and/or the plug 3 to be driven so as to fix more securely the positioning of the implant while it is being put into place and so as to facilitate dismantling of the ancillary appliance without moving the implant.

Figure 8:
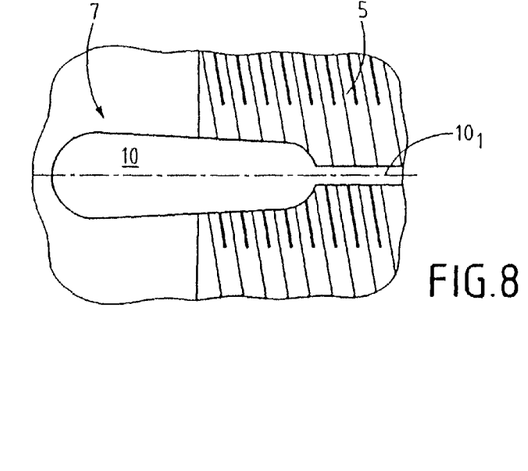

In the embodiments shown with four branches 5, said cage 1 has four slots 10 forming inter-branch spaces as shown in FIG. 3 looking along arrow VIII of FIG. 9, for example. Such slots serve firstly to improve fusion of the bone graft that may be housed in the inside volume 9 with the adjacent intervertebral disks, and secondly to obtain better deformation of the branches 5 during installation of the implant, the branches in this particular portion being of section that is smaller than at their ends. In addition, such slots can be oblong in shape with their ends situated towards the distal ends of the branches 5 being narrower than their opposite ends, as shown in FIG. 8, and terminating in a narrow slit $10_1$ between the distal ends of adjacent pairs of said branches. Such a shape, at least for the main slot 10, makes it possible to have a slot with parallel edges, once the cage has been expanded. In addition, choosing a profile of this shape instead of an initial slot of constant width as shown in FIG. 3A, makes it possible to increase the bearing surface area between the spacer 2 and the distal ends of the branches 5 of the cage, thus providing greater strength.

Figures 1, 2:
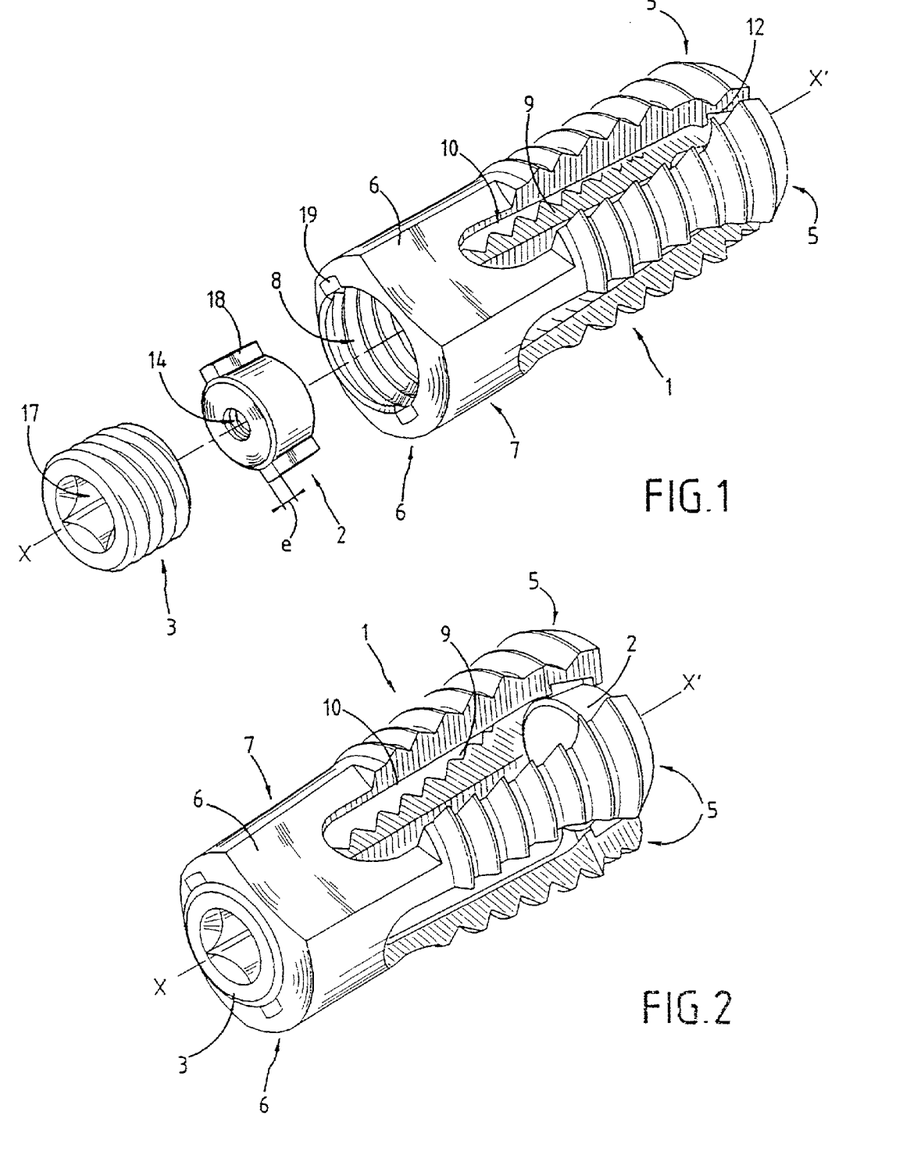
FIG. 1 is a perspective view of an example of an implant in the "rest" position with its various parts in alignment on a common installation axis XX'.
FIG. 2 is a perspective view of the FIG. 1 implant in its "active" position with the above three parts assembled together.
Figure 12A:
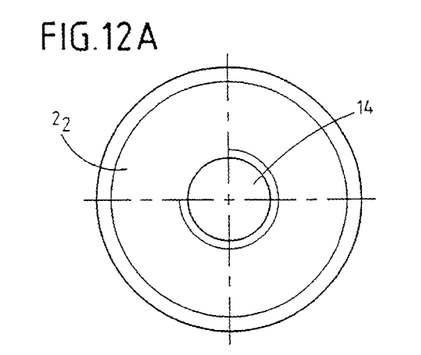
FIGS. 12, 13, and 14 are a face view and a section view respectively of: a non-screw end spacer for the embodiment of FIGS. 1, 2, 9, 10, and 11; a screw end and/or intermediate spacer for an embodiment of FIGS. 3, 4, and 5, and a closure plug for any of the embodiments of the invention.
Figure 12B:
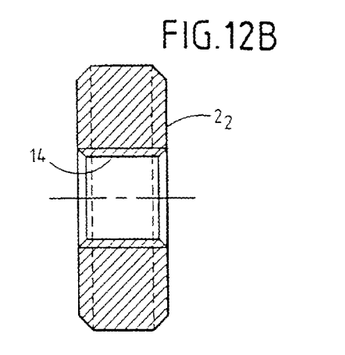

In the embodiments of FIGS. 1, 2, 9, 10, and 11, the inside surfaces of the branches 5 defining the inside volume 9 of the cage 1 are smooth, so the volume then includes at its distal end an axial housing 12 suitable for receiving said spacer $2_2$ as shown in FIG. 12, and for holding it by means of a shoulder 13 of greater diameter than that of the inside volume 9 of the cage in its active position, as shown in FIG. 1.

Said spacer $2_2$ has a threaded axial bore 14 suitable for receiving a rod whose end at least is likewise threaded and compatible for the purpose of putting the spacer into place merely by applying thrust and by being moved in translation, with said installation rod being subsequently removable.

In FIGS. 1 and 2, in order to avoid any risk of the body of the cage 1 deforming at its anterior end near the distal ends of the branches 5 under large stresses due to pressure from adjacent vertebrae, which could have the effect of moving branches towards one another by sliding around the spacer 2, it is possible to provide the spacer with at least two splines 18 or other means that are disposed symmetrically about the axis XX' of the implant. Such a spacer is either put into place inside the cage 1 before the implant is put into place by being engaged therein from the ends of the branches, or else the seat 7 has at least two compatible grooves 19 allowing the said two splines 18 to slide therealong when the spacer 2 is put into place if it needs to be inserted via the seat, the width e of the splines being no greater than the distance and the spacing between the distal ends of two adjacent branches 5.

The device may include additional systems so that the branches do not deform after they have been expanded, for example an outside ring received in a groove at the ends of the branches and deformable by the branches.

Figure 13A:
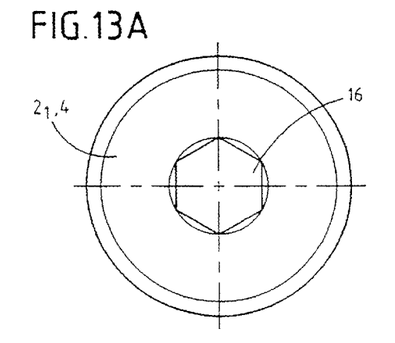
Figure 13B:
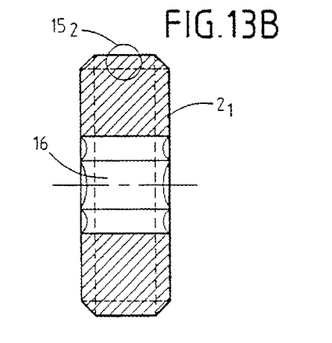

In the embodiment shown in FIGS. 3, 4, and 5, the inside surfaces of the branches 5 defining the inside volume 9 of the cage 1 are threaded with a pitch equivalent to that of the orifice 8 in the seat 7, e.g. as shown in FIG. 6, and said spacer $2_1$ is threaded in compatible manner, as shown in FIGS. 13A and 13B.

In this embodiment with an inside thread, said cage 1 may also include at least one other intermediate spacer 4 threaded like the end spacer $2_1$ and capable of being screwed behind it in order firstly to compress the bone matter that may have been inserted in the space defined between the two spacers, and secondly to stiffen the central portion of the cage.

Said end and intermediate spacers $2_1$ and 4 have respective polygonal axial orifices 16 suitable for receiving a removable rod having a male end of compatible shape so as to drive them while they are being installed.

The frustoconical shape of the inside volume 9 of the cage 1 may have a half-angle of slope $\alpha$ lying in the range 6° to 9°, for example.

The invention claimed is:

1. An implant for inserting between two vertebrae and for providing proper vertebral spacing, the implant comprising:
    a base having a proximal end and a distal end;
    at least three branches attached to the distal end of the base and extending in a distal direction away from the base, the base and the branches forming a hollow cage defining an internal volume, each branch having an inward side and an outward side;
    a spacer sized to fit within the cage and adapted to move along the inward side of each branch upon the urging of an implant-installing instrument, the spacer having a thickness substantially less than the length of the cage, said spacer and cage being sized so that each branch will move to an extended position when the spacer is urged in the distal direction from the base toward a distal end of the implant along the inward side of each branch by the implant-installing instrument;
    an aperture formed in the base extending from the internal volume of the cage and through the base to an outward end of the base, the aperture adapted to allow the implant-installing instrument to be inserted through the base to engage the spacer within the cage; and
    a plug that is removably attached to the proximal end of the base to prevent graft material inside the cage from escaping via the proximal end,
    wherein a substantial portion of the internal volume is empty after insertion of the spacer, and said portion is substantially larger than the portion of the internal volume occupied by structure of the implant, thereby permitting insertion of the graft material in an amount sufficient to achieve vertebral fusion.

2. The implant of claim 1, wherein the spacer has dimensions that are compatible with the dimension of the base.

3. The implant of claim 1, wherein the distal end of each branch is adapted to removably receive the spacer to securely maintain the extended position of each branch.

4. The implant of claim 1, wherein the hollow cage is configured to be filled at least partially with bone matter.

5. The implant of claim 1, wherein a width of the spacer is larger than at least a portion of an interior of the hollow cage in its unexpanded state, whereby the branches are moved to the extended position when the spacer is advanced along the inward side of the branches.

6. The implant of claim 1, wherein the spacer is generally disc-shaped.

7. The implant of claim 6, wherein the spacer has at least two wings, each wing adapted to fit between adjacent branches.

8. The implant of claim 1, wherein at least a portion of the inward side of each branch is essentially tapered.

9. The implant of claim 1, wherein at least a portion of the outward side of the branch comprises a plurality of grooves formed therein to provide better anchoring to the vertebrae.

10. The implant of claim 9, wherein each branch has a distal end and wherein the hollow cage has slots forming inter-branch spaces to improve fusion of the graft material with adjacent intervertebral disks and wherein the slots become narrower at the distal ends of the branches.

11. The implant of claim 1, wherein each branch has a distal end and wherein the hollow cage has slots forming inter-branch spaces to improve fusion of the graft material with adjacent intervertebral disks and wherein the slots become narrower at the distal ends of the branches.

12. An implant for inserting between two vertebrae and for providing proper vertebral spacing, the implant comprising:
    a proximal seat with a hole formed therein at a proximal end and at least three branches extending distally from the seat forming a hollow cage, each branch having a length, an inward side facing an interior of the cage, and an outward side facing away from the cage;
    a spacer located at or near an end of the implant adapted to be moved by an implant-installing rod and having an aperture sized to communicate with the implant-installing rod, and the spacer being removable from the implant-installing rod, the spacer having a thickness substantially less than the length of the cage, said spacer and cage being sized so that the branches will bend when the spacer is placed in contact with the inward side and urged by the implant-installing rod across the length of each branch in a direction extending from the proximal seat of the implant toward a distal end of the branches, and
    a plug that is removably attached to the proximal end of the proximal seat to prevent graft material inside the cage from escaping via the proximal end,
    wherein the proximal seat, the branches, and the spacer define an interior space that is substantially empty when the implant-installing rod is removed; and
    wherein the hole formed in the proximal seat is adapted to allow the implant-installing rod to be inserted through the proximal seat to engage the spacer within the cage.

13. An implant for inserting between two vertebrae and for providing proper vertebral spacing, the implant comprising:
    a proximal seat with a hole formed therein at a proximal end and at least three branches extending distally from the seat forming a hollow cage, each branch having a length, an inward side facing an interior of the cage, and an outward side facing away from the cage; and
    a spacer located at or near an end of the implant adapted to be moved by an implant-installing rod and having an aperture sized to communicate with the implant-installing rod, and the spacer being removable from the implant-installing rod, the spacer having a thickness substantially less than the length of the cage, said spacer and cage being sized so that the branches will bend when the spacer is placed in contact with the inward side and urged by the implant-installing rod across the length of each branch in a direction extending from the proximal seat of the implant toward a distal end of the branches,
    a plug that is removably attached to the proximal end of the proximal seat to prevent graft material inside the cage from escaping via the proximal end,
    wherein the proximal seat, the branches, and the spacer define an interior space that is substantially empty when the implant-installing rod is removed,
    wherein the hole formed in the proximal seat is adapted to allow the implant-installing rod to be inserted through the proximal seat to engage the spacer within the cage, and
    wherein each branch has a distal end and wherein the hollow cage has slots forming inter-branch spaces to improve fusion of the graft material with adjacent intervertebral disks and wherein the slots become narrower at the distal ends of the branches.

14. An implant for inserting between two vertebrae and for providing proper vertebral spacing, the implant comprising:
- a base with a hole at a proximal end and at least three branches extending distally from the base forming a hollow cage having an inside volume, each branch having an inward side facing an interior of the cage and an outward side facing away from the cage, and at least a portion of the outward side of each branch having a plurality of grooves formed therein;
- a spacer sized to fit within the cage and adapted to slide along the inward side of each branch, the spacer having a thickness substantially less than the length of the cage, wherein the spacer and the cage are sized and configured so that the branches will bend from a normal position to an extended position when the spacer is advanced, from a position near the base toward a distal end of the branches, and
- a plug that is removably attached to the proximal end of the base to prevent graft material inside the cage from escaping via the proximal end,
- wherein the inside volume of the cage between the hole and the spacer does not contain any portion of the implant, and
- wherein the hole is configured to allow an implant installation instrument to be inserted through the base to engage the spacer in the cage.

15. An implant for inserting between two vertebrae and for providing proper vertebral spacing, the implant comprising:
- a base with a hole at a proximal end and at least three branches extending distally from the base forming a hollow cage having an inside volume, each branch having an inward side facing an interior of the cage and an outward side facing away from the cage, and at least a portion of the outward side of each branch having a plurality of grooves formed therein;
- a spacer sized to fit within the cage and adapted to slide along the inward side of each branch, the spacer having a thickness substantially less than the length of the cage, wherein the spacer and the cage are sized and configured so that the branches will bend from a normal position to an extended position when the spacer is advanced, from a position near the base toward a distal end of the branches, and
- a plug that is removably attached to the proximal end of the base to prevent graft material inside the cage from escaping via the proximal end,
- wherein the inside volume of the cage between the hole and the spacer does not contain any portion of the implant,
- wherein the hole is configured to allow an implant installation instrument to be inserted through the base to engage the spacer in the cage, and
- wherein the spacer is generally disc-shaped.

* * * * *